United States Patent [19]

Leishman

[11] Patent Number: 4,848,569
[45] Date of Patent: Jul. 18, 1989

[54] APPARATUS AND METHOD FOR DISPOSING OF CONTAMINATED NEEDLES

[76] Inventor: Layne S. Leishman, 19121 Yacht La., Huntington Beach, Calif. 92646

[21] Appl. No.: 247,041

[22] Filed: Sep. 20, 1988

[51] Int. Cl.$^4$ ............................................ B65D 83/10
[52] U.S. Cl. .................................... 206/365; 206/366; 206/363; 206/367
[58] Field of Search .............. 206/362, 494, 499, 365, 206/366, 367; 221/34

[56] References Cited

U.S. PATENT DOCUMENTS

| | | | |
|---|---|---|---|
| 1,999,879 | 4/1935 | Leg | 206/445 |
| 3,637,072 | 1/1972 | Narusawa et al. | 206/365 |
| 3,876,067 | 4/1975 | Schwarz | 206/366 |
| 4,365,709 | 12/1982 | Lestea | 206/362 |

*Primary Examiner*—Joseph Man-Fu Moy
*Attorney, Agent, or Firm*—Gordon L. Peterson; Loyal M. Hanson

[57] ABSTRACT

An apparatus includes a magazine for containing a plurality of shields so that a user can insert the tip of a hypodermic needle into one of the shields and then slide the shield out of the magazine means as a protective cover over the tip. A plurality of penetrable shields are provided within the magazine. The magazine includes an elongated structure defining a passage having an open end and an outwardly opening channel that extends along the passage to the open end. The passage is dimensioned and arranged to receive the penetrable so that the shields can be individually slid along the passage and out of the open end for dispensing purposes. The channel is dimensioned and arranged so that a user can insert the tip of the hypodermic needle through the channel and into a selected one of the shields and then slide the selected shield along the passage and out of the open end by moving the hypodermic needle along the channel.

17 Claims, 1 Drawing Sheet

APPARATUS AND METHOD FOR DISPOSING OF CONTAMINATED NEEDLES

BACKGROUND OF THE INVENTION

1. Technical Field

This invention relates generally to medical equipment, and more particularly to protective shielding for a used hypodermic needle.

2. Background Information

Contact with the pointed end of a used hypodermic needle risks exposure to the AIDS virus and hepatitis. Emergencies and high stress operative procedures increase the risk. Thus, those working with or near such pointed instruments share concern over the protective shielding scheme employed.

A hypodermic syringe typically includes a tubular shield over the needle. It can be replaced after use, but the passage into the shield is of small diameter and the shield must be inserted over the sharp end of the needle. As a result, the risk of accidental contact with a contaminated needle point is substantial.

Other known shielding arrangements may be rather complex and inconvenient to use. Still others involve a specially made syringe. Consequently, there is a need for a new and improved apparatus and method for disposing of contaminated needles that overcome these concerns.

SUMMARY OF THE INVENTION

This invention solves the problems outlined above with a magazine of penetrable shields from which individual shields can be easily dispensed. Immediately after withdrawing a needle from the patient, the user sticks the tip into one of the shields, slides the shield out of the magazine, and disposes of the needle and shield together. If desired, the magazine can be mounted on an accessible support structure, such as a wall, where the shields are readily available as needed.

Thus, a specially made syringe is not required. In addition, the magazine and shields are more conveniently and inexpensively manufactured. Moreover, they can be readily mounted at a selected point of use to keep a supply of shields available. Their use is extremely straightforward and convenient, and the risk of contacting a contaminated needle is substantially reduced.

Generally, an apparatus constructed according to a major aspect of the invention includes a magazine for containing a plurality of shields so that a user can insert the tip of a hypodermic needle into one of the shields and then slide the shield out of the magazine means as a protective cover over the tip. A supply of penetrable shields are provided within the magazine. The magazine may be composed of a plexiglass material, for example, and the shields may take the form of flexible vinyl blocks that the tip can penetrate.

The magazine includes an elongated structure defining both a passage having a first open end and an outwardly opening channel extending along the passage to the first open end. The passage is dimensioned and arranged to receive the penetrable shields so that the shields can be individually slid along the passage and out of the first open end for dispensing purposes. The channel is dimensioned and arranged so that a user can insert the tip of the hypodermic needle through the channel and into a selected one of the shields and then slide the selected shield along the passage and out of the first open end by moving the hypodermic needle along the channel.

According to another aspect of the invention, there is provided a mounting member for mounting the magazine means on a support structure. For this purpose, the magazine may have runners that slide between flanges on the mounting member, and the mounting member may be provided with an adhesive strip that enables convenient attachment to a vertical support surface.

In line with the above, a method of protecting the tip of a hypodermic needle after use includes providing a magazine containing a supply of penetrable shields. The magazine is configured to enable a user to insert the tip of a hypodermic needle into a selected one of the shields and then slide the selected shield out of the magazine means by moving the hypodermic needle.

With the loaded magazine at hand, the method proceeds by grasping a hypodermic needle having a tip to be protected. Next, the tip is inserted into a selected one of the shields while the shield is within the magazine. Then, the selected shield is slid out of the magazine. This results in far less risk of the user contacting the tip.

The above mentioned and other objects and features of this invention and the manner of attaining them will become apparent, and the invention itself will be best understood, by reference to the following description taken in conjunction with the accompanying illustrative drawings.

DESCRIPTION OF THE PREFERRED EMBODIMENTS

Figure 1:
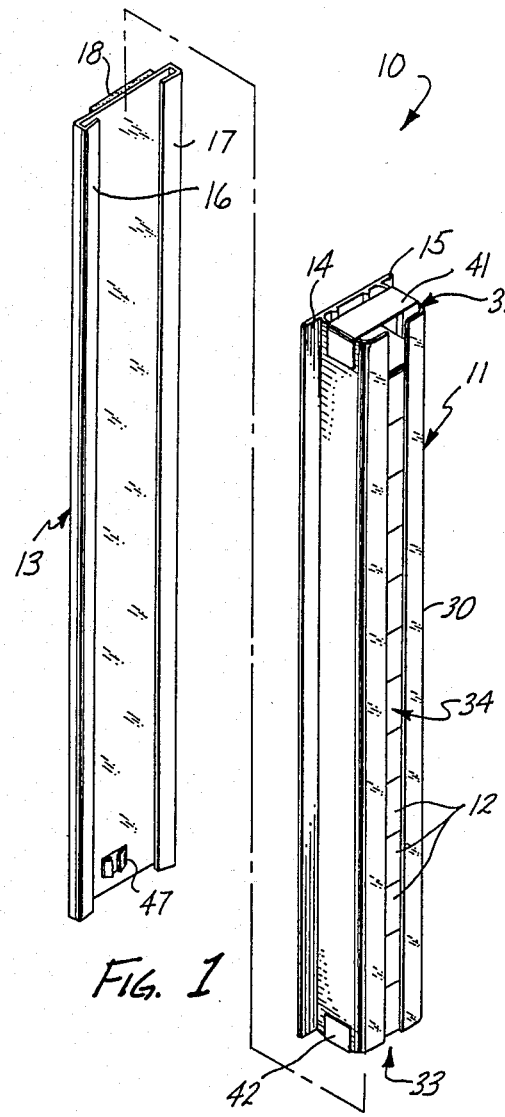
FIG. 1 of the drawings is a perspective view an apparatus or magazine of shields constructed according to the invention showing use with a mounting strip provided according to another aspect of the invention.

Referring now to the drawings, there is shown an apparatus 10 constructed according to the invention. Generally, the apparatus 10 includes a magazine 11 and a supply of shields 12 within the magazine 11 (FIGS., 1-4). Mounting means, such as a mounting member 13 in FIGS. 1-4, may be included.

Figure 4:
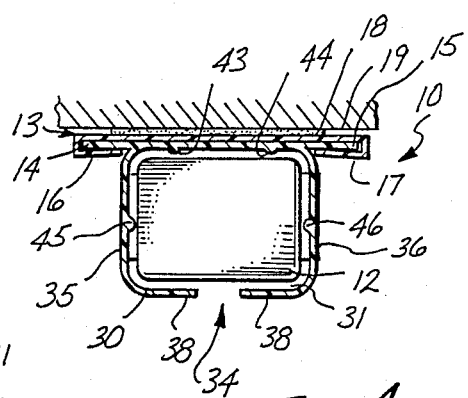
FIG. 4 is an enlarged cross sectional view of the magazine of shields taken on line 4—4 of FIG. 2.

Runners 14 and 15 on the magazine 11 are engaged by respective ones of flanges 16 and 17 on the mounting member 13 to secure the magazine 11 to the mounting member 13, and an adhesive strip 18 attached to the mounting member 13 secures the mounting member to a support structure, such as a wall 19 in FIG. 4.

Considering the magazine 11 in further detail, it is configured to contain a supply of shields and enable a user to insert the distal end portion or tip of a hypodermic needle into a selected one of the shields and then slide the selected shield out of the magazine mean by moving the hypodermic needle.

This is illustrated in FIG. 1 with a syringe 20 having a barrel portion 21 and a hypodermic needle 22 attached to the barrel portion 21. As illustrated, a distal end portion or tip 23 of the hypodermic needle 21 that is to be protected is inserted at least partially into a selected one of the shields 12, preferably the uppermost one 12' (FIG. 2).

Then, the user grasps the hypodermic needle 22. This is intended to mean that the user grasps the barrel portion 21 of the syringe 20 (or other structure to which the needle is attached). Of course, the user can conceivable grasp the needle directly.

Figure 2:
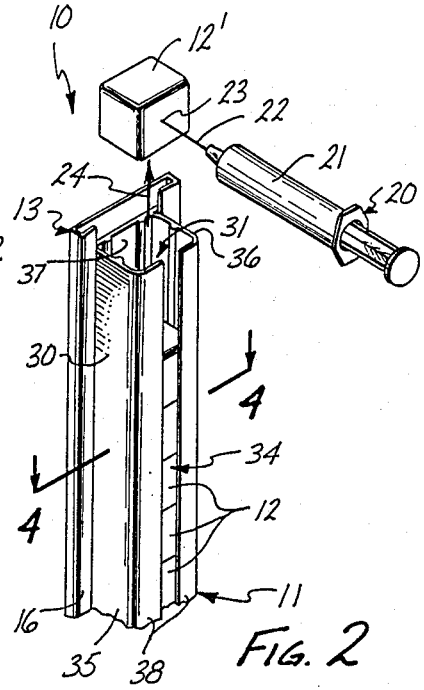
FIG. 2 is perspective view of a portion of the magazine of shields mounted on the mounting strip showing removal of a shield from the magazine.

While grasping the hypodermic needle 22, the user inserts the tip 23 into the uppermost shield 12' while the shield 12' is within the magazine 11, and then slides the shield 12' out of the magazine 11 by moving the hypodermic needle 22 and shield 12' in the direction of an arrow 24 in FIG. 2.

In order to contain the shields 12, the magazine 11 includes an elongated structure 30 defining a passage 31 having first and second open ends 32 and 33 an outwardly opening channel 34 that extends along the passage 31 to the first open end 32. The passage 31 is dimensioned and arranged to receive the penetrable shields 12 so that the shields can be individually moved or slid along the passage 31 and out of the first open end 32 for dispensing purposes.

The magazine includes confronting first and second side walls 35 and 36 and confronting third and fourth sidewalls 37 and 38. These combine to define the passage, the illustrated passage 31 having a rectangularly shaped cross section extending from the first open end 32 to the oppositely disposed second open end 33 that is designed to receive rectangularly shaped shields. Of course, other shapes for the passage and the shields may be employed within the broader inventive concepts disclosed, the rectangular shape being conveniently fabricated.

In addition, the passage 31 is dimensioned and arranged so that the shields 12 fit loosely within the passage 31, thereby enabling the user to lift a selected one of the shields 12 out of the magazine 11 with the hypodermic needle 22 in the manner illustrated in FIG. 2. The illustrated passage 31 is generally straight for this purpose. It need not be, however, within the broader inventive concepts disclosed.

The magazine 11 can take any of various shapes and sizes and still function to contain a supply of shields and enable their removal in the manner described above. In this regard, however, the straight configuration illustrated is conveniently and inexpensive manufactured by injection molding techniques, for example. If desired, a long length of magazine stock can be produced so that magazines having any of various selected lengths can be cut from it.

As an idea of size, the illustrated magazine 11 is about one inch wide across the runners 14 and 15, and about six to twelve inches long. The passage is dimensioned to receive shields measuring about six-tenths inch by about five-tenths inch, and the precise length may be such that the magazine 11 will hold a dozen one-half inch thick shields, for example.

Once the magazine is fabricated, it is loaded with a supply of shields and strips 41 and 42 of a suitable material such as an adhesive tape are affixed over respective ones of the open ends 32 and 33, the strips 41 and 42 serving as means for preventing the shields from sliding out of the first and second open ends. Preferably, the shields are rectangular blocks of a suitable penetrable material that can be penetrated by the tip 23 of the hypodermic needle 22, such as a flexible vinyl material that is somewhat denser and less penetrable than a foam material. Once the magazine 11 is ready for use, the user simply removes the strip 34. Other known means of preventing the shields from sliding out may be employed, such as rigid clips or caps over the open ends 32 and 33.

The channel 34 is defined by the fourth sidewall 38 and it is dimensioned and arranged so that a user can insert the tip 23 of the hypodermic needle 22 through the channel 34 and into a selected one of the shields 12. In addition, the channel 34 extends along the passage 31 to the first open end 32 so that the user can slide the selected shield along the passage 31 and out of the first open end 32 by moving the hypodermic needle 22 along the channel 34. The illustrated channel 34 is about two-tenths inch wide for this purpose, but dimension is not critical.

Figure 3:
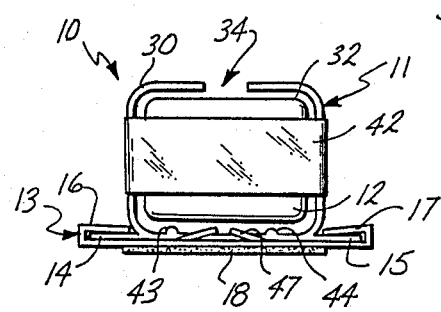
FIG. 3 is an enlarged view of the bottom end of the magazine of shields.

In order to reduce drag on the shields 12 as they are slid along the passage 31, at least one of the sidewalls 35-38 includes an inwardly protruding, longitudinally extending rib that limits the amount of contact between the shields 12 and the sidewall. Preferably, a plurality of ribs 43-46 are provided for this purpose (FIGS. 3 and 4).

The magazine 11 can be used without mounting it on a wall. It can be laid on a table, for example. In order to use the magazine 11 with the mounting member 13, however, the user secures the mounting member 13 to a support structure, such as a table for horizontal use or, preferably, a vertical surface for vertical use. This is done utilizing the adhesive strip 18. Of course, other known means such as screws can be used.

The mounting member 13 is about as along as the magazine 11, and the flanges 16 and 17 are spaced apart sufficiently to slidably receive and engage the runners 14 and 15. The user slides the runners 14 and 15 along the flanges 16 and 17 until the magazine 11 contacts a stop structure 47 on the mounting member (FIG. 1). The stop structure 47 may take any of various suitable forms, such as a pair of ears bent outwardly from the mounting member, and it serves to limit the distance the runners 14 and 15 can be slid into the flanges 16 and 17.

Thus, this invention alleviates the concerns over contaminated needles with a magazine of penetrable shields from which individual shields can be easily dispensed. A specially made syringe is not required. The magazine and shields are more conveniently and inexpensively manufactured. They can be readily mounted at a selected point of use to keep a supply of shields available. Their use is extremely straightforward and convenient, and the risk of contacting a contaminated needle is substantially reduced.

Although an exemplary embodiment of the invention has been shown and described, many changes, modifications, and substitutions may be made by one having ordinary skill in the art without necessarily departing from the spirit and scope of the invention. In that regard, the term "hypodermic needle" is intended to include any of various other pointed needles and instruments, such as an IV needle, a trocar, or the like, so that use with any such other devices falls within the scope of the claims.

What is claimed is:

1. An apparatus, comprising:
    magazine means for containing a plurality of shields so that a user can insert the tip of a hypodermic needle into one of the shields and then slide the shield out of the magazine means as a protective cover over the tip; and a plurality of penetrable shields within the magazine means;

the magazine means including an elongated structure defining a passage having a first open end and an outwardly opening channel that extends along the passage to the first open end;

the passage being dimensioned and arranged to receive the penetrable shields so that the shields can be individually slid along the passage and out of the first open end for dispensing purposes; and the channel being dimensioned and arranged so that a user can insert the tip of the hypodermic needle through the channel and into a selected one of the shields and then slide the selected shield along the passage and out of the first open end by moving the hypodermic needle along the channel.

2. An apparatus as recited in claim 1, wherein the elongated structure includes:

confronting first and second side walls and confronting third and fourth sidewalls that are connected together to define the passage.

3. An apparatus as recited in claim 2, wherein:

the passage has a rectangularly shaped cross section extending from the first open end to an oppositely disposed second open end; and the channel extends between the first and second open ends.

4. An apparatus as recited in claim 3, further comprising:

means for preventing the penetrable shields from sliding out of the second open end.

5. An apparatus as recited in claim 4, wherein the means for preventing the penetrable shields from sliding out of the second open end includes:

a strip of tape affixed to the elongated structure over the second open end.

6. An apparatus as recited in claim 5, further comprising:

means for preventing the penetrable shields from sliding out of the first open end during shipment.

7. An apparatus as recited in claim 6, wherein the means for preventing the penetrable shields from sliding out of the first open end during shipment includes:

a strip of tape affixed to the elongated structure over the first open end.

8. An apparatus as recited in claim 2, wherein:

at least one of the sidewalls includes an inwardly protruding, longitudinally extending rib that limits the amount of contact between the shields and the sidewall.

9. An apparatus as recited in claim 1, wherein each of the shields includes:

a block of penetrable material.

10. An apparatus as recited in claim 1, wherein:

each of the penetrable shields is composed of a vinyl material.

11. An apparatus as recited in claim 1, wherein:

each of the penetrable shields is rectangularly shaped.

12. An apparatus as recited in claim 1, further comprising:

mounting means for mounting the magazine means on a support structure.

13. An apparatus as recited in claim 12, wherein the mounting means includes:

a mounting member;

means for securing the magazine on the mounting member; and means for securing the mounting member to the support surface.

14. An apparatus as recited in claim 13, wherein the means for securing the magazine on the mounting member includes:

first and second runners extending longitudinally along the magazine; and first and second flanges extending longitudinally along the mounting member in positions to slidably engage the runners.

15. An apparatus as recited in claim 14, wherein the mounting member includes:

means for limiting the distance the first and second runners can be slid into the first and second flanges.

16. An apparatus as recited in claim 13, wherein the means for securing the mounting member to the support surface includes:

a strip of adhesive material affixed to the mounting member.

17. A method of protecting the tip of a hypodermic needle after it has penetrated a human body and been removed, comprising:

providing magazine means containing plurality of shields, the magazine means being configured to enable a user to insert the tip of a hypodermic needle into a selected one of the shields and then slide the selected shield out of the magazine means by moving the hypodermic needle;

manually inserting the tip of a hypodermic needle into a selected one of the shields while the shield is within the magazine; and sliding the selected one of the shields out of the magazine.

* * * * *